United States Patent
Naya

(10) Patent No.: US 6,577,396 B1
(45) Date of Patent: Jun. 10, 2003

(54) SURFACE PLASMON SENSOR

(75) Inventor: Masayuki Naya, Kanagawa-ken (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/315,024

(22) Filed: May 20, 1999

(30) Foreign Application Priority Data

May 21, 1998 (JP) .......................................... 10-139621

(51) Int. Cl.$^7$ .............................................. G01N 21/55
(52) U.S. Cl. ...................................................... 356/445
(58) Field of Search ................................ 356/445, 138; 385/12, 13

(56) References Cited

U.S. PATENT DOCUMENTS

| | | | | |
|---|---|---|---|---|
| 4,844,613 A | * | 7/1989 | Batchelder et al. .......... | 356/445 |
| 4,889,427 A | * | 12/1989 | Van Veen et al. ........... | 356/445 |
| 5,341,215 A | * | 8/1994 | Seher .......................... | 356/445 |
| 5,561,069 A | * | 10/1996 | Brigham-Burke et al. .... | 385/12 |
| 5,644,069 A | * | 7/1997 | Liu et al. .................... | 324/609 |
| 5,875,032 A | | 2/1999 | Naya ........................... | 356/445 |

FOREIGN PATENT DOCUMENTS

| | | | | |
|---|---|---|---|---|
| JP | 5-240787 | 9/1993 | | |
| JP | 6-167443 | 6/1994 | ......... | G01N/21/27 |
| JP | 8-7458 | 1/1996 | | |
| JP | 9-33427 | 1/1997 | | |

\* cited by examiner

*Primary Examiner*—Zandra V Smith
(74) *Attorney, Agent, or Firm*—Sughrue Mion, PLLC

(57) ABSTRACT

A surface plasmon sensor includes a dielectric block, a metal film which is formed on one face of the dielectric block and is brought into contact with a sample, a light source emitting a light beam and an optical system which causes the light beam to enter the dielectric block and converges the light beam on the interface of the dielectric block and the metal film so that components of the light beam impinge upon the interface at various angles including angles of total reflection. An array of a plurality of photodetector elements extending in a predetermined direction and positioned detect is positioned so that the components of the light beam reflected at the interface in total reflection at various angles are received by the respective photodetector elements. Light detecting signals output from the photodetector elements are differentiated with respect to the direction of the array of the photodetector elements, and the reflecting angle at which the intensity of the light reflected at the interface takes a minimum value is determined on the basis of the differential values.

9 Claims, 3 Drawing Sheets

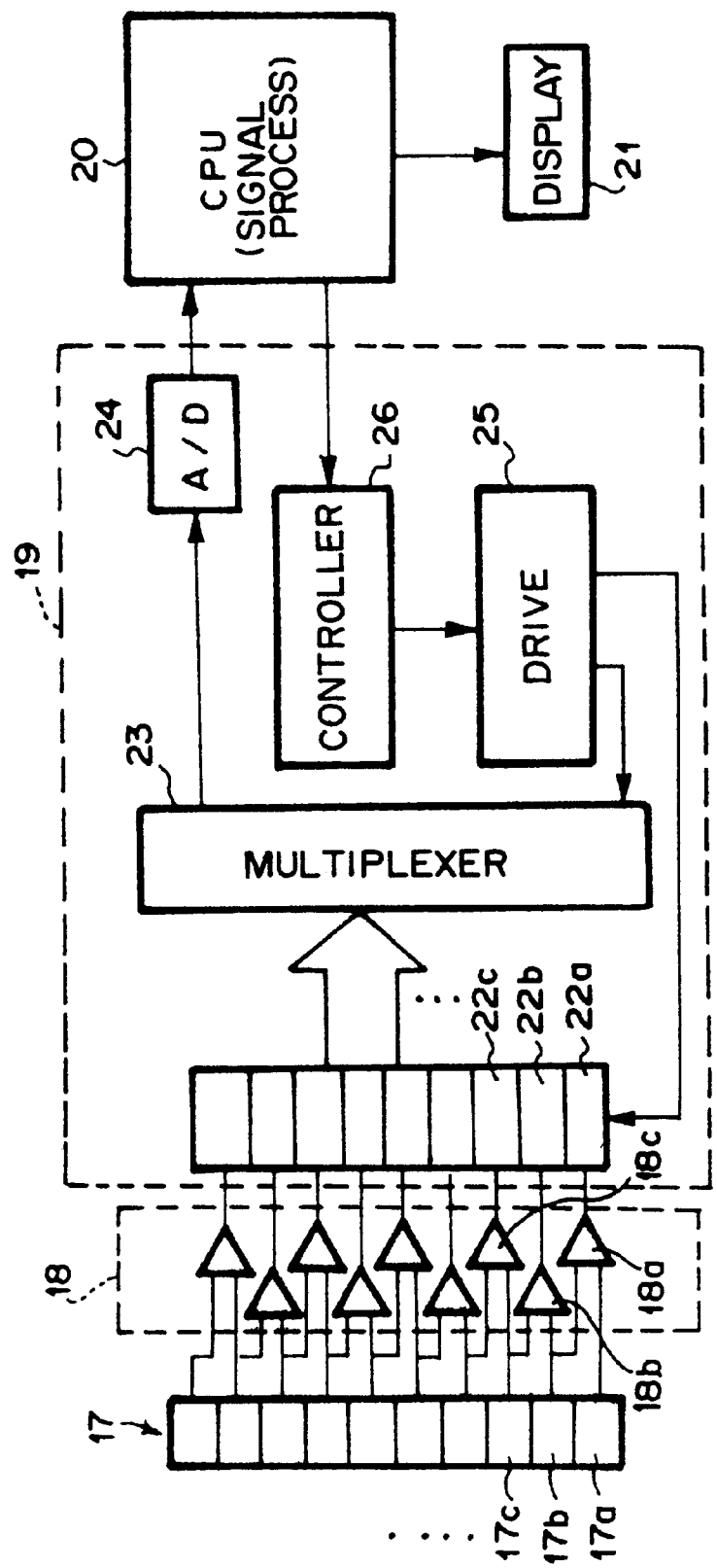
F I G. 2

F I G. 3A
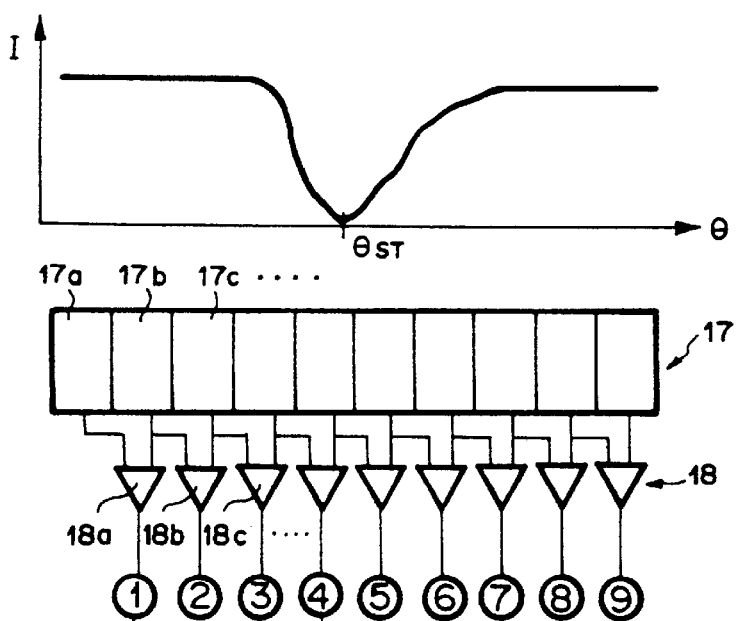
F I G. 3B
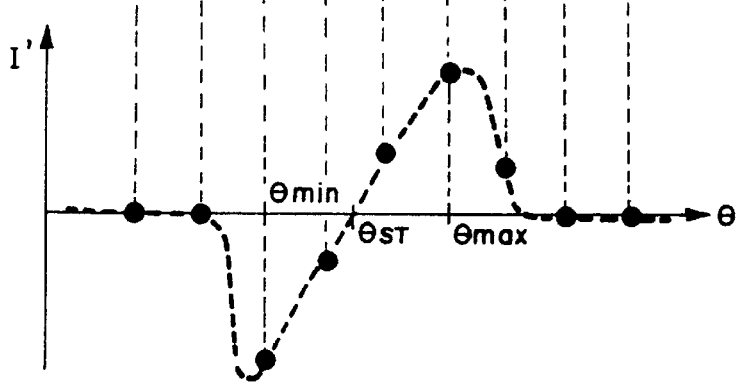

SURFACE PLASMON SENSOR

BACKGROUND OF THE INVENTION

1. Field of the Invention

This invention relates to a surface plasmon sensor for quantitatively analyzing a material in a sample utilizing generation of surface plasmon, and more particularly to a surface plasmon sensor in which the photodetecting portion is improved.

2. Description of the Related Art

In metal, free electrons vibrate in a group to generate compression waves called plasma waves. The compression waves generated in a metal surface are quantized into surface plasmon.

There have been proposed various surface plasmon sensors for quantitatively analyzing a material in a sample utilizing a phenomenon that such surface plasmon is excited by light waves. Among those, one employing a system called "Kretschmann configuration" is best known. See, for instance, Japanese Unexamined Patent Publication No. 6(1994)-167443.

The plasmon sensor using the Kretschmann configuration basically comprises a dielectric block shaped, for instance, like a prism, a metal film which is formed on one face of the dielectric block and is brought into contact with a sample, a light source emitting a light beam, an optical system which causes the light beam to enter the dielectric block so that the light beam is reflected in total reflection at the interface of the dielectric block and the metal film and various angles of incidence of the light beam to the interface of the dielectric block and the metal film including an angle of incidence at which surface plasmon is generated can be obtained, and a photodetector means which is able to detect the intensity of the light beam reflected in total reflection from the interface for the various angles of incidence.

In order to obtain various angles of incidence of the light beam to the interface, a relatively thin incident light beam may be caused to impinge upon the interface while deflecting the incident light beam or a relatively thick incident light beam may be caused to converge on the interface so that components of the incident light beam impinge upon the interface at various angles. In the former case, the light beam which is reflected from the interface at an angle which varies as the incident light beam is deflected may be detected by a photodetector which is moved in synchronization with deflection of the incident light beam or by an area sensor extending in the direction in which reflected light beam is moved as a result of deflection. In the latter case, an area sensor which extends in directions so that all the components of light reflected from the interface at various angles can be detected by the area sensor may be used.

In such a plasmon sensor, when a light beam impinges upon the metal film at a particular angle of incidence θsp not smaller than the angle of total internal reflection, evanescent waves having an electric field distribution are generated in the sample in contact with the metal film and surface plasmon is excited in the interface between the metal film and the sample. When the wave vector of the evanescent waves is equal to the wave number of the surface plasmon and wave number matching is established, the evanescent waves and the surface plasmon resonate and light energy is transferred to the surface plasmon, whereby the intensity of light reflected in total reflection from the interface of the dielectric block and the metal film sharply drops.

When the wave number of the surface plasmon can be known from the angle of incidence θsp at which the phenomenon of attenuation in total reflection takes place, the dielectric constant of the sample can be obtained. That is, $$Ksp(\varpi) = \frac{\varpi}{c} \sqrt{\frac{\epsilon_m(\varpi)\epsilon_s}{\epsilon_m(\varpi) + \epsilon_s}}$$

wherein Ksp represents the wave number of the surface plasmon, ω represents the angular frequency of the surface plasmon, c represents the speed of light in a vacuum, and εm and εs respectively represent the dielectric constants of the metal and the sample.

When the dielectric constant εs of the sample is known, the concentration of a specific material in the sample can be determined on the basis of a predetermined calibration curve or the like. Accordingly, a specific component in the sample can be quantitatively analyzed by detecting the angle of incidence θsp at which the intensity of light reflected in total reflection from the interface of the prism and the metal film sharply drops (This angle of incidence θsp will be referred to as "the total reflection cancel angle", hereinbelow).

In the conventional plasmon sensor of the type described above, the intensity of the light beam reflected in total reflection from the interface for the various angles of reflection is detected by a photodetector which is moved in synchronization with deflection of the incident light beam, or an area sensor extending in the direction in which reflected light beam is moved as a result of deflection.

In the case of the former, though a relatively wide dynamic range can be ensured with respect to measurement of the total reflection cancel angle, it becomes difficult to effect analysis of the sample at a high speed since a mechanical drive mechanism for driving the photodetector becomes necessary.

In the case of the latter, though high speed analysis can be realized, it is difficult to ensure high accuracy in analysis since the area sensor such as a CCD is narrow in dynamic range for resolution and charge accumulation.

We have proposed an arrangement for detecting the total reflection cancel angle θsp in which the amount of reflected light in a first reflecting angle range and the amount of reflected light in a second reflecting angle range are separately detected by a pair of photodetectors such as the segments of a two-segment photodiode and the total reflection cancel angle θsp is obtained on the basis of a comparison of the outputs of the photodetectors. See Japanese Unexamined Patent Publication No. 9(1997)-292334.

With this arrangement, the total reflection cancel angle θsp can be obtained at high sensitivity. However, in this case, measurement of the total reflection cancel angle θsp becomes impossible when the total reflection cancel angle θsp varies beyond the range where the photodetectors can receive the reflected light and as a result, the dynamic range is only 2 to 3° at most.

SUMMARY OF THE INVENTION

In view of the foregoing observations and description, the primary object of the present invention is to provide a surface plasmon sensor in which the total reflection cancel angle θsp can be measured at a sufficiently high accuracy with a wide dynamic range.

The surface plasmon sensor of the present invention comprises a dielectric block shaped, for instance, like a prism, a metal film which is formed on one face of the dielectric block and is brought into contact with a sample, a light source emitting a light beam, an optical system which causes the light beam to enter the dielectric block and converges the light beam on the interface of the dielectric block and the metal film so that components of the light beam impinge upon the interface at various angles including angles of total reflection, a photodetector means which consists of an array of a plurality of photodetector elements extending in a predetermined direction and is positioned so that the components of the light beam reflected at the interface in total reflection at various angles are received by the respective photodetector elements, a differential means which differentiates light detecting signals output from the photodetector elements with respect to the direction of the array of the photodetector elements, and an operation means which determines the reflecting angle at which the intensity of the light reflected at the interface takes a minimum value on the basis of the differential values of the light detecting signals.

Preferably, the operation means is arranged to determine the reflecting angle at which the intensity of the light reflected at the interface takes a minimum value by interpolating a plurality of differential values in the range between the reflecting angle at which the differential value takes a maximum value and that at which the differential value takes a minimum value and determining the position in the direction of the array of the photodetector elements in which the differential value is zero.

As the differential means, one which obtains the difference between the light detecting signals output from a pair of adjacent photodetector elements can be suitably used. Further as the photodetector means, a photodiode array may be suitably used.

In the surface plasmon sensor with the arrangement described above, the incident angle θ of the light beam to the interface of the dielectric block and the metal film corresponds to the position of the photodetector means in the direction of the array of the photodetector elements in one-to-one correspondence. Further, the intensity of the reflected light takes a minimum value at the total reflection cancel angle θsp.

The position of the photodetector means in the direction of the array of the photodetector elements in which the intensity of the reflected light takes a minimum value can be determined on the basis of the differential values obtained by differentiating the light detecting signals output from the photodetector elements with respect to the direction of the array of the photodetector elements. That is, the differential value becomes zero in the position of the photodetector means in the direction of the array of the photodetector elements in which the intensity of the reflected light takes a minimum value.

Accordingly, the incident angle θ of the light beam in one-to-one correspondence to the position of the photodetector means in the direction of the array of the photodetector elements in which the intensity of the reflected light takes a minimum value is the total reflection cancel angle θsp, and a specific component in the sample can be quantitatively analyzed on the basis of the total reflection cancel angle θsp.

Further since a photodiode array or the like is used as the photodetector means for detecting the intensity of the reflected light, the total reflection cancel angle θsp can be measured at a high sensitivity.

Further since the array of the photodetector elements extends in the direction in which the total reflection cancel angle θsp varies, the total reflection cancel angle θsp can be detected even if it varies by a large amount so long as the variation is within the range where the array of the photodetector elements extends, which range can be theoretically extends as long as desired. Thus, in the surface plasmon sensor of the present invention, the total reflection cancel angle θsp can be measured with a wide dynamic range.

Further, in the surface plasmon sensor of the present invention, since detection of the intensity of the reflected light requires no drive mechanism, analysis of the sample can be effected at a high speed.

BRIEF DESCRIPTION OF THE DRAWINGS

FIG. 2 is a block diagram showing the electrical arrangement of the surface plasmon sensor, FIG. 3A is a graph showing the relation between the angle of incidence of a light beam and the intensity of the reflected light, and FIG. 3B is a graph showing the relation between the angle of incidence of a light beam and the differential value of the light detecting signal.

DESCRIPTION OF THE PREFERRED EMBODIMENTS

Figure 1:
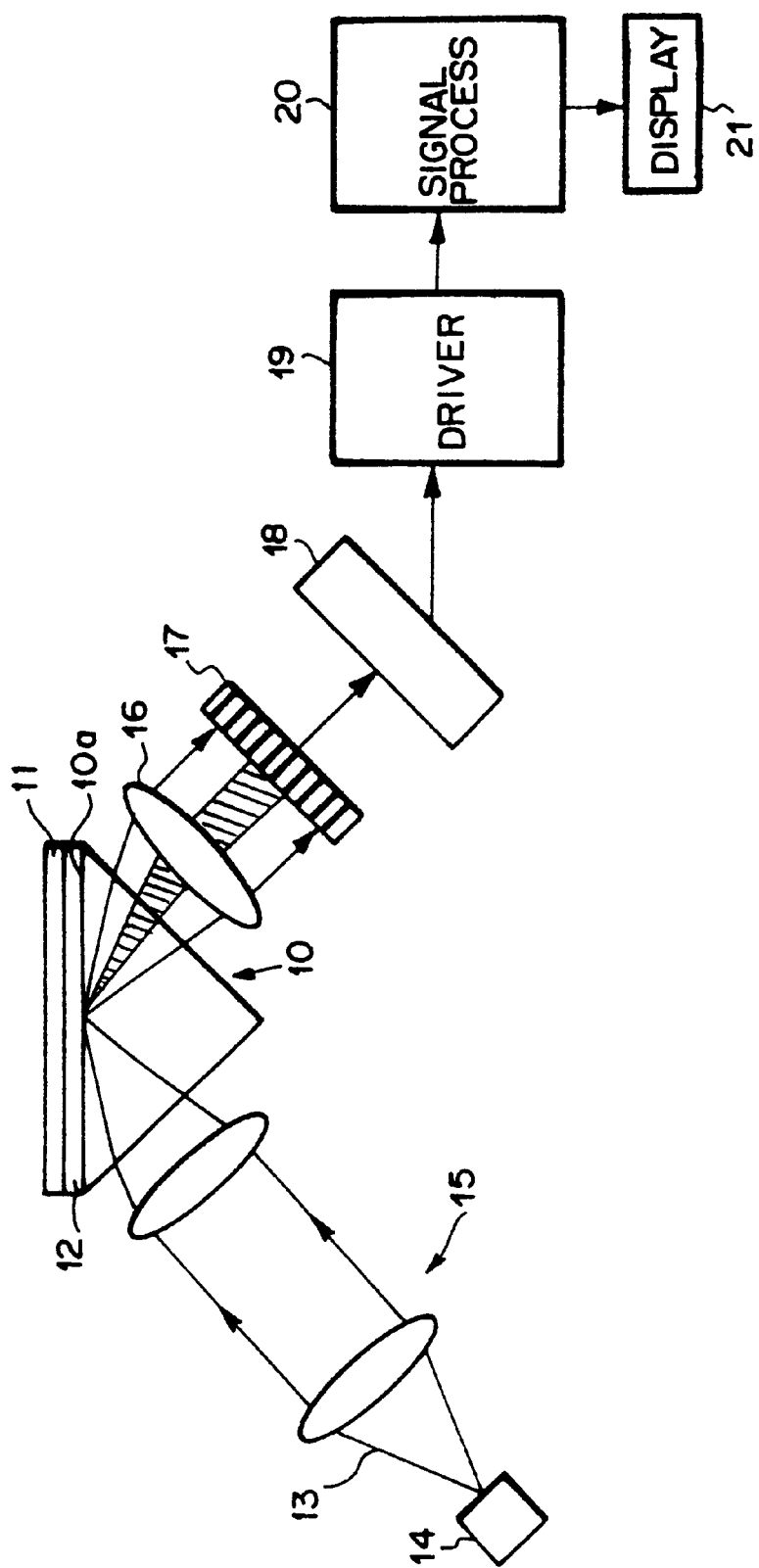
FIG. 1 is a side view of a surface plasmon sensor in accordance with an embodiment of the present invention.

In FIG. 1, a surface plasmon sensor in accordance with an embodiment of the present invention comprises a triangular prism 10 having a major axis extending in a direction perpendicular to the surface of the paper, a metal film 12 such as of gold, silver or the like which is formed on one face (the upper face as seen in FIG. 1) of the prism 10 and brought into contact with a sample 11, a semiconductor laser 14 emitting a single light beam (laser beam) 13, an optical system 15 which causes the light beam 13 to enter the prism 10 so that various angles of incidence of the light beam 13 to the interface 10a of the prism 10 and the metal film 12 can be obtained, a collimator lens 16 which collimates the light beam 13 reflected in total reflection at the interface 10a, a photodetector means 17 which detects the light beam 13 collimated by the collimator lens 16, a differential amplifier array 18 connected to the photodetector means 17, a driver 19, a signal processing section 20 such as of a computer system, and a display means 21 connected to the signal processing section 20.

As shown in FIG. 2, the differential amplifier array 18 comprises a plurality of differential amplifiers 18a, 18b, 18c . . . The driver 19 comprises a plurality of sample holding circuits 22a, 22b, 22c . . . which sample-hold the outputs of the differential amplifiers 18a, 18b, 18c . . . , a multiplexer 23 into which the outputs of the sample holding circuits 22a, 22b, 22c . . . are input, an A/D convertor 24 which digitizes the output of the multiplexer 23 and inputs the same into the signal processing section 20, a drive circuit 25 which drives the multiplexer 23 and the sample holding circuits 22a, 22b, 22c . . . , and a controller 26 which controls the drive circuit 25 on the basis of instruction from the signal processing section 20.

As shown in FIG. 1, the light beam 13 emitted from the light source 14 as divergent light is converged on the interface 10a of the prism 10 and the metal film 12 in a plane perpendicular to the major axis of the prism 10 by the optical system 15. Accordingly the light beam 13 impinging upon the interface 10a contains components which impinge upon the interface 10a at various angles θ. The angle of incidence θ is made not smaller than an angle of total internal reflection. The light beam 13 is reflected in total reflection at the interface 10a and accordingly the reflected light beam 13 contains components which are reflected at the interface 10a at various angles.

The light beam 13 reflected in total reflection at the interface 1a and collimated by the collimator lens 16 is detected by the photodetector means 17. In this embodiment, the photodetector means 17 is a photodiode array comprising a plurality of photodiodes 17a, 17b, 17c . . . which are arranged in a row. The photodiodes 17a, 17b, 17c . . . are arranged in a direction substantially perpendicular to the direction of travel of the collimated light beam 13 in a plane perpendicular to the major axis of the prism 10. Accordingly, the components of the light beam 13 reflected in total reflection at various reflecting angles at the interface 10a are detected by different photodiodes 17a, 17b, 17c . . . .

The outputs of the respective photodiodes 17a, 17b, 17c . . . are input into the respective differential amplifiers 18a, 18b, 18c . . . At this time, the output of each photodiode is input into the corresponding differential amplifier together with the output of a photodiode adjacent thereto. Accordingly, the outputs of the differential amplifiers 18a, 18b, 18c . . . are equivalent to the values obtained by differentiating the light detecting signals output from the photodiodes 17a, 17b, 17c . . . with respect to the direction of array of the photodiodes 17a, 17b, 17c . . . .

The outputs of the differential amplifiers 18a, 18b, 18c . . . are held by the sample holding circuits 22a, 22b, 22c . . . at predetermined timings and input into the multiplexer 23. The multiplexer 23 inputs the outputs of the differential amplifiers 18a, 18b, 18c . . . held by the sample holding circuits 22a, 22b, 22c . . . into the A/D convertor 24 in sequence in a predetermined order. The A/D convertor 24 digitizes the outputs of the differential amplifiers 18a, 18b, 18c . . . and inputs them into the signal processing section 20.

FIG. 3A shows the relation between the angle of incidence θ of the light beam 13 to the interface 10a and the intensity I of the light beam 13 reflected in total reflection at the interface 10a.

As described before, a light beam impinging upon the interface 10a at a particular angle of incidence θsp excites surface plasmon in the interface 10a, and the intensity I of the light reflected from the interface 10a at an angle corresponding to the angle θsp greatly drops. This particular angle of incidence θsp is the total reflection cancel angle and the intensity I of the reflected light takes a minimum value at the total reflection cancel angle θsp.

As shown in FIG. 3B, the photodiodes 17a, 17b, 17c . . . correspond in one-to-one correspondence to angles of incidence θ.

The relation between the positions of the photodiodes 17a, 17b, 17c . . . in the direction of array thereof, i.e., the angle of incidence θ, and the output I' of the differential amplifiers 18a, 18b, 18c . . . (the differential value of the intensity I of the reflected light) is as shown in FIG. 3B.

The signal processing section 20 determines the total reflection cancel angle θsp on the basis of the differential values I' input from the A/D convertor 24. In this embodiment, the signal processing section 20 determines the angle θsp at which the differential value I' becomes zero by interpolating a plurality of differential values I' in the range between the angle of incidence θmax at which the differential value I' takes a maximum value and that θmin at which the differential value I' takes a minimum value.

The signal processing section 20 causes the display means 21 to display the total reflection cancel angle θsp thus determined. Otherwise it is possible to arrange the signal processing section 20 to quantitatively analyze a specific material in the sample on the basis of the total reflection cancel angle θsp and a predetermined calibration curve or the like. In this case, the result of the quantitative analysis is displayed by the display means 21 substantially in real time.

As can be understood from the description above, in the surface plasmon sensor of this embodiment, the total reflection cancel angle θsp can be measured at a sufficiently high accuracy with a wide dynamic range for the reason described above.

What is claimed is:

1. A surface plasmon sensor comprising
    a dielectric block,
    a metal film which is formed on one face of the dielectric block and is brought into contact with a sample,
    a light source emitting a light beam,
    an optical system which causes the light beam to enter the dielectric block and converges the light beam on the interface of the dielectric block and the metal film so that components of the light beam impinge upon the interface at various angles of incidence including angles of total reflection,
    a photodetector means which consists of an array of a plurality of photodetector elements extending in a predetermined direction and is positioned so that each of the components of the light beam reflected at the interface in total reflection at various angles are received by the respective photodetector elements in one-to-one correspondence, and so that each photodetector element measures surface plasmon resonance and outputs a light detecting signal,
    a comparator means which compares the light detecting signals output from each of the photodetector elements with respect to the direction of the array of the photodetector elements, and
    an operation means which determines the reflecting angle at which the intensity of the light reflected at the interface takes a minimum value on the basis of the result of comparison of the light detecting signals.

2. A surface plasmon sensor as defined in claim 1 in which the comparator means differentiates the light detecting signals output from the photodetector elements with respect to the direction of the array of the photodetector elements, and
    the operation means determines the reflecting angle at which the intensity of the light reflected at the interface takes a minimum value on the basis of the differential values of the light detecting signals.

3. A surface plasmon sensor as defined in claim 2 in which the operation means is arranged to determine the reflecting angle at which the intensity of the light reflected at the interface takes a minimum value by interpolating a plurality of differential values in the range between the reflecting angle at which the differential value takes a maximum value and that at which the differential value takes a minimum value and determining the position in the direction of the array of the photodetector elements in which the differential value is zero.

4. A surface plasmon sensor as defined in claim 2 in which the comparator means obtains the difference between the light detecting signals output from a pair of adjacent photodetector elements.

5. A surface plasmon sensor as defined in claim 2 in which the photodetector means comprises a photodiode array.

6. A surface plasmon sensor comprising:
   a dielectric block,
   a metal film which is formed on one face of the dielectric block and is brought into contact with a sample,
   a light source emitting a light beam,
   an optical system which causes the light beam to enter the dielectric block and converges the light beam on the interface of the dielectric block and the metal film so that components of the light beam impinge upon the interface at various angles of incidence including angles of total reflection,
   a photodetector means which consists of an array of a plurality of photodetector elements extending in a predetermined single direction and is positioned so that each of the components of the light beam reflected at the interface in total reflection at various angles are received by the respective photodetector elements in one-to-one correspondence, and so that each photodetector element measures surface plasmon resonance and outputs a light detecting signal,
   a comparator means which comprises a plurality of differential amplifiers and a plurality of sample holding circuits for comparing the light detecting signals output from the photodetector elements with respect to the direction of the array of the photodetector elements, each of said plurality of differential amplifiers being provided for a pair of adjacent photodetector elements to obtain the difference between the light detecting signals output from the pair of adjacent photodetector elements, the outputs of said plurality of differential amplifiers being held by said plurality of sample holding circuits at predetermined timings, and
   an operation means which determines the reflecting angle at which the intensity of the light reflected at the interface takes a minimum value on the basis of the result of comparison of the light detecting signals.

7. A surface plasmon sensor as defined in claim 6 in which the operation means is arranged to determine the reflecting angle at which the intensity of the light reflected at the interface takes a minimum value by interpolating a plurality of differential values in the range between the reflecting angle at which the differential value takes a maximum value and that at which the differential value takes a minimum value and determining the position in the direction of the array of the photodetector elements in which the differential value is zero.

8. A surface plasmon sensor as defined in claim 6 in which the photodetector means comprises a photodiode array.

9. A surface plasmon sensor as defined in claim 7 in which the photodetector means comprises a photodiode array.

* * * * *